US00PP31211P3

(12) United States Plant Patent
Schoone

(10) Patent No.: US PP31,211 P3
(45) Date of Patent: Dec. 10, 2019

(54) *PHALAENOPSIS* PLANT NAMED 'WHITE MOLLIE'

(50) Latin Name: *Phalaenopsis hybrida*
Varietal Denomination: White Mollie

(71) Applicant: FLORICULTURA B.V., Heemskerk (NL)

(72) Inventor: Rene Schoone, Assendelft (NL)

(73) Assignee: Floricultura B.V., Heemskerk (NL)

( * ) Notice: Subject to any disclaimer, the term of this patent is extended or adjusted under 35 U.S.C. 154(b) by 0 days.

(21) Appl. No.: 16/350,079

(22) Filed: Sep. 21, 2018

(65) Prior Publication Data

US 2019/0098819 P1 Mar. 28, 2019

Related U.S. Application Data

(60) Provisional application No. 62/561,902, filed on Sep. 22, 2017.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — C. A. Whealy

(57) ABSTRACT

A new and distinct cultivar of *Phalaenopsis* plant named 'White Mollie', characterized by its upright growth habit; relatively short dark green-colored leaves; strong and relatively long flowering stems; freely flowering habit with typically about four racemes per plant, each inflorescence with numerous flowers; and white-colored flowers with yellow-colored labellum.

2 Drawing Sheets

Botanical designation: *Phalaenopsis hybrida.*
Cultivar denomination: 'WHITE MOLLIE'.

BACKGROUND OF THE INVENTION

The present invention relates to a new and distinct cultivar of *Phalaenopsis* plant, botanically known as *Phalaenopsis hybrida*, known by the breeder's reference 291434 and hereinafter referred to by the name 'White Mollie'.

The new *Phalaenopsis* plant is a product of a planned breeding program conducted by the Inventor in Heemskerk, The Netherlands. The objective of the breeding program is to develop new rapid growing and freely flowering *Phalaenopsis* plants with good leaf shape and unique and attractive flower patterns and coloration.

The new *Phalaenopsis* plant originated from a cross-pollination in 2005 in Heemskerk, The Netherlands of *Phalaenopsis hybrida* 'Alabaster', not patented, as the female, or seed, parent with *Phalaenopsis hybrida* ('Snow Tiger x Funny Virgin'), not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in 2013.

Asexual reproduction of the new *Phalaenopsis* plant by in vitro meristem propagation in a controlled environment in Heemskerk, The Netherlands since July, 2013 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'White Mollie'. These characteristics in combination distinguish 'White Mollie' as a new and distinct *Phalaenopsis* plant:

1. Upright plant habit.
2. Moderately vigorous to vigorous growth habit.
3. Relatively short dark green-colored leaves.
4. Strong and relatively long flowering stems.
5. Freely flowering habit with typically about four racemes per plant, each inflorescence with numerous flowers.
6. White-colored flowers with yellow-colored labellum.

Plants of the new *Phalaenopsis* can be compared to plants of the female parent, 'Alabaster'. Plants of the new *Phalaenopsis* differ primarily from plants of 'Alabaster' in flower color as plants of the new *Phalaenopsis* have yellow-colored labellum whereas plants of 'Alabaster' have brown-colored labellum.

Plants of the new *Phalaenopsis* can be compared to plants of the male parent, ('Snow Tiger x Funny Virgin'). Plants of the new *Phalaenopsis* differ primarily from plants of ('Snow Tiger x Funny Virgin') in flower size as plants of the new *Phalaenopsis* have larger flowers than plants of ('Snow Tiger x Funny Virgin').

Plants of the new *Phalaenopsis* can be compared to plants of *Phalaenopsis hybrida* 'Tropic Snowball', not patented. In side-by-side comparisons, plants of the new *Phalaenopsis* differ primarily from plants of 'Tropic Snowball' in flower color as flowers of the new *Phalaenopsis* have yellow-colored labellum whereas flowers of plants of 'Tropic Snowball' have lighter yellow-colored labellum. In addition, labellum of plants of the new *Phalaenopsis* are more "open" than labellum of plants of 'Tropic Snowball'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'White Mollie' grown in a container.

The photograph at the top of second sheet is a close-up view of a typical flower of 'White Mollie'.

DETAILED BOTANICAL DESCRIPTION

The aforementioned photographs and following observations and measurements describe plants grown during the late summer in 10-cm containers in a glass-covered greenhouse in Heemskerk, The Netherlands and under cultural practices typically used in commercial *Phalaenopsis* production. During the production of the plants, day temperatures ranged from 20° C. to 22° C. and night temperatures averaged 18° C. and light levels ranged from 5 klux to 10 klux. Plants were three years old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'White Mollie'.

Parentage:

- *Female parent.—Phalaenopsis hybrida* 'Alabaster', not patented.
- *Male parent.—Phalaenopsis hybrida* ('Snow Tiger x Funny Virgin'), not patented.

Propagation:

- *Type*.—By in vitro meristem propagation.
- *Time to initiate roots, summer and winter*.—About two weeks at temperatures about 28° C. to 30° C.
- *Time to produce a rooted young plant, summer and winter*.—About 20 to 25 weeks at temperatures about 28° C. to 30° C.
- *Root description*.—Fine, fibrous; typically light yellowish white in color, actual color of the roots is dependent on substrate composition, water quality, fertilizer, substrate temperature and age of roots.
- *Rooting habit*.—Freely branching; medium density.

Plant description:

- *Plant form and growth habit*.—Herbaceous epiphyte; upright plant habit with typically about four racemes per plant, each inflorescence with numerous flowers; monopodial; moderately vigorous to vigorous growth habit and moderate growth rate.
- *Plant height, substrate level to top of foliar plane*.—About 12.3 cm.
- *Plant height, substrate level to top of inflorescences*.—About 43.1 cm.
- *Plant diameter or spread*.—About 32.5 cm.

Leaf description:

- *Arrangement and quantity*.—Distichous, simple; sessile; about seven per plant.
- *Length*.—About 24.3 cm.
- *Width*.—About 6.8 cm.
- *Aspect*.—Horizontal to slightly upright and arching.
- *Shape*.—Narrowly obovate to narrowly oblong; slightly carinate.
- *Apex*.—Broadly acute, unequal.
- *Base*.—Sheathing.
- *Margin*.—Entire; slightly revolute to non-revolute.
- *Texture and luster, upper and lower surfaces*.—Smooth, glabrous; slightly glossy.
- *Venation pattern*.—Camptodromous.
- *Color*.—Developing leaves, upper surface: Close to 143A. Developing leaves, lower surface: Close to 144A. Fully expanded leaves, upper surface: Close to 137B; venation, close to NN137B. Fully expanded leaves, lower surface: Close to between 144A and 146B; towards the margins, close to between 143A and 146A; venation, close to 143C.

Inflorescence description:

- *Appearance and flowering habit*.—Showy zygomorphic flowers arranged on axillary simple or branched racemes; typically about four racemes per plant; each inflorescence with about eight open flowers; flowers face outwardly on arching inflorescences supported by upright peduncles; flowers with three petals, two lateral petals and one center petal transformed into a labellum and three sepals.
- *Fragrance*.—None detected.
- *Time to flower*.—Plants begin flowering about two months after flower bud initiation.
- *Flower longevity*.—Long flowering period, individual flowers maintain good substance for about four to six months on the plant; flowers not persistent.
- *Inflorescence length (lowermost flower to inflorescence apex)*.—About 15.9 cm.
- *Inflorescence width*.—About 13.8 cm.
- *Flower buds*.—Height: About 2 cm. Diameter: About 1.5 cm. Shape: Broadly ovate. Color: Close to 145D and 150D; proximally, close to 145C.
- *Flower diameter*.—About 7.9 cm by 8.5 cm.
- *Flower depth*.—About 2.7 cm.
- *Petals, quantity and arrangement*.—Three, two lateral petals and one center petal transformed into a labellum.
- *Lateral petals*.—Length: About 4.2 cm. Width: About 4.9 cm. Shape: Reniform to broadly reniform. Apex: Obtuse. Margin: Entire. Texture and luster, upper and lower surfaces: Smooth, glabrous, velvety; matte. Color: When opening, upper surface: Close to NN155D. When opening, lower surface: Close to NN155D; center, close to NN155A. Fully opened, upper and lower surfaces: Close to NN155D to lighter than NN155D; color does not change with development.
- *Labellum*.—Appearance: Tri-lobed with two lateral lobes and a central lobe. Length, lateral lobe: About 2 cm. Width, lateral lobes: About 1.4 cm. Length, central lobe: About 3.1 cm. Width, central lobe: About 2.1 cm. Shape, lateral lobes: Obovate. Shape, central lobe: Deltoid. Apex, lateral lobes: Obtuse. Apex, central lobe: Cleft with two moderately long recurved cirrose tips, about 1.8 cm in length and about 1.2 cm in width. Margins, lateral lobes: Entire;

moderately undulate. Margins, central lobe: Entire. Texture and luster, upper and lower surfaces: Smooth, glabrous, velvety; matte. Callosities: Located at the base of the labellum and attachment point of the lateral petals; about 4 mm in length, about 6 mm in width and about 5 mm in height. Color: When opening, upper surface: Lateral lobes: Close to NN155D; distal margins tinged with close to 157D; proximal margins, close to 7B; basal stripes, close to 61A. Central lobe: Close to NN155B; mid-section, close to 5B to 5C; distal margins, close to 163C; base, close to NN155D; stripes, close to 61A. Callosities: Close to 4B to 4C; fine dots, close to 61A. When opening, lower surface: Lateral lobes: Close to NN155D; distal margins tinged with close to 157D; proximal margins, close to 7B. Central lobe: Close to NN155B; central band, close to 145C to 145D; mid-section, close to 1B to 1C; distal margins, close to 163C; base, close to NN155A. Fully opened, upper surface: Lateral lobes: Close to NN155D; distal margins, close to 155A; proximal margins, close to 12A; basal stripes, close to 61A. Central lobe: Close to NN155B; mid-section, close to 12B to 12C; distal margins, close to 163A to 163B; base, close to NN155D; stripes, close to 61A. Callosities: Close to 11D; fine dots, close to 61A. Fully opened, lower surface: Lateral lobes: Close to NN155D; distal margins tinged with close to between 155C and 157D; proximal margins, close to 12A. Central lobe: Close to NN155B; central band, close to 155C; mid-section, close to 5B; distal margins, close to 163A to 163B; base, close to NN155A.

*Sepals*.—Quantity and arrangement: Three, two lower lateral sepals and one upper dorsal sepal. Length, lateral sepal: About 4.4 cm. Width, lateral sepals: About 2.6 cm. Length, dorsal sepal: About 4.5 cm. Width, dorsal sepal: About 3.1 cm. Shape, lateral sepals: Ovate; slightly concave. Shape, dorsal sepal: Ovate to elliptic; slightly concave. Apex, lateral sepal: Broadly and bluntly acute to narrowly obtuse. Apex, dorsal sepals: Obtuse. Base, lateral and dorsal sepals: Truncate. Margin, lateral and dorsal sepals: Entire. Texture and luster, lateral and dorsal sepals, upper and lower surfaces: Smooth, glabrous, velvety; matte. Color: When opening, upper surface: Lateral sepals: Close to 155C; fading towards the base to close to 157D; fine dots, basal, close to 61A. Dorsal sepals: Close to NN155B; fading toward the margins and apex to close to NN155C to NN155D. When opening, lower surface: Lateral sepals: Close to 145C to 145D; fading towards the margins and apex to close to 155C. Dorsal sepals: Close to 157D; fading towards the margins and apex to close to N155B. Fully opened, upper surface: Lateral sepals: Close to NN155C; fading towards the margins and apex to close to NN155D; fine dots, basal, close to 70B; color does not change with development. Dorsal sepals: Close to NN155D. Fully opened, lower surface: Lateral sepals: Close to 157D; fading towards the margins and apex to close to NN155D; color does not change with development. Dorsal sepals: Close to NN155D.

*Peduncles*.—Length: About 43.7 cm. Diameter: About 5 mm. Strength: Very strong. Aspect: Upright to about 35° from vertical. Texture and luster: Smooth, glabrous; matte. Color: Close to 137B.

*Pedicels*.—Length: About 3.3 cm. Diameter: About 3.5 mm. Strength: Moderately strong. Aspect: About 65° from peduncle axis. Texture and luster: Smooth, glabrous; matte. Color: Close to 145A; distally, fading to close to N155B; proximally, fading to close to 144B.

*Reproductive organs*.—Androecium: Column length: About 8 mm. Column width: About 6 mm. Column color: Close to NN155D. Pollinia quantity: Two. Pollinia diameter (per two pollinia): About 2 mm. Pollinia color: Close to 24A. Gynoecium: Stigma length: About 3 mm. Stigma width: About 4 mm. Stigma shape: Reniform. Stigma color: Close to NN155C. Ovary length: About 8 mm. Ovary diameter: About 1 mm. Ovary color: Close to lighter than 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 10° C. to about 40° C. and to be suitable for USDA Hardiness Zone 10.

It is claimed:

1. A new and distinct *Phalaenopsis* plant named 'White Mollie' as illustrated and described.

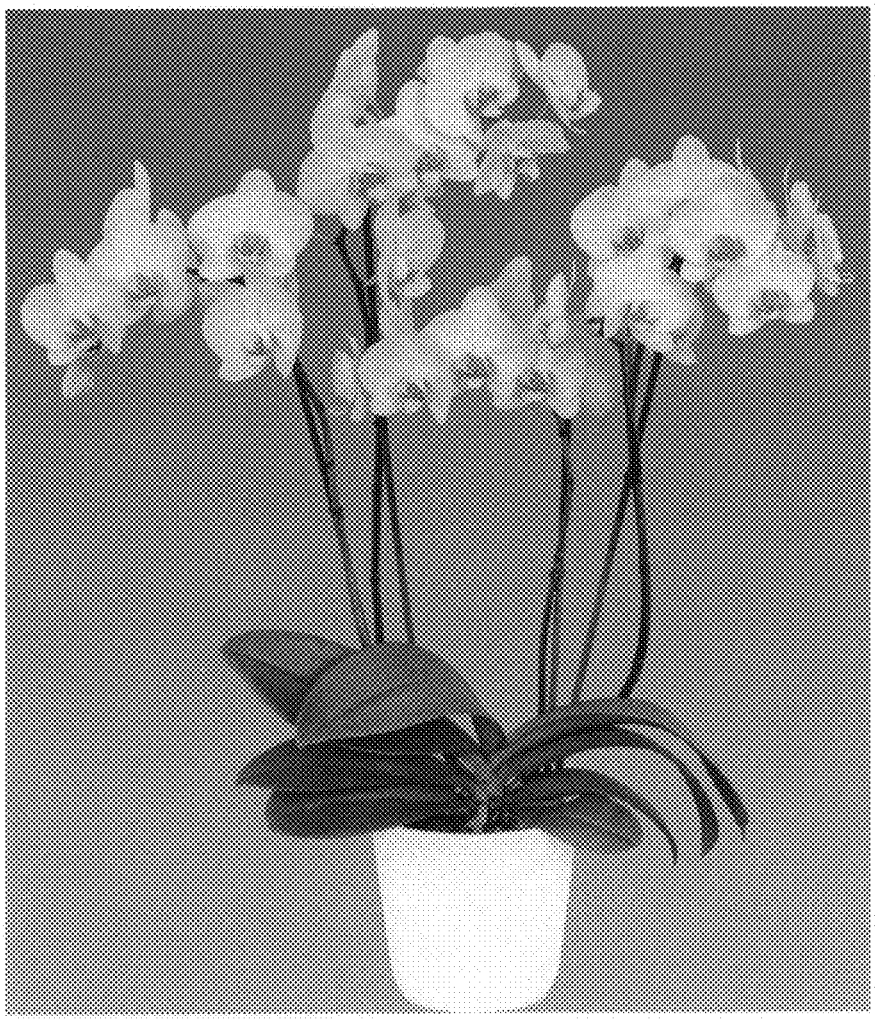

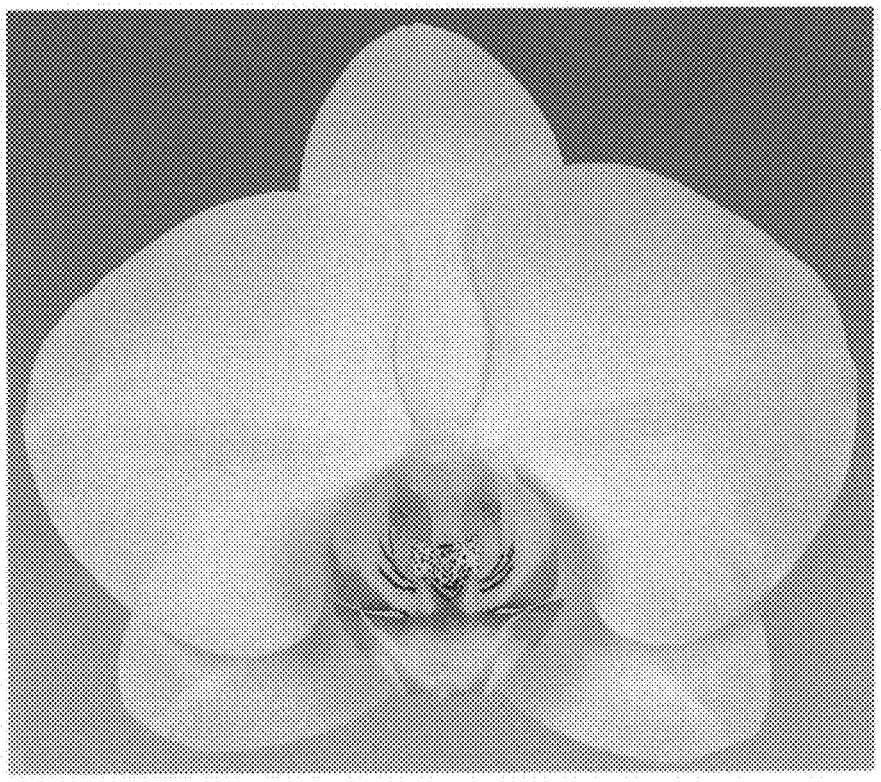

* * * * *